(12) United States Patent
Yu et al.

(10) Patent No.: US 7,252,894 B2
(45) Date of Patent: Aug. 7, 2007

(54) ANTHRACENE COMPOUND FOR ORGANIC ELECTROLUMINESCENT DEVICE

(75) Inventors: Chen-Ping Yu, Longtan Township, Taoyuan County (TW); Chung-Wen Ko, Sijhih (TW)

(73) Assignee: AU Optronics Corp., Hsinchu (TW)

( * ) Notice: Subject to any disclaimer, the term of this patent is extended or adjusted under 35 U.S.C. 154(b) by 247 days.

(21) Appl. No.: 10/946,895

(22) Filed: Sep. 22, 2004

(65) Prior Publication Data

US 2005/0260442 A1 Nov. 24, 2005

(30) Foreign Application Priority Data

May 24, 2004 (TW) .............................. 93114612 A

(51) Int. Cl.
H01L 51/50 (2006.01)
C09C 211/00 (2006.01)
C09K 11/06 (2006.01)

(52) U.S. Cl. ............... 428/690; 428/917; 313/504; 313/506; 564/427; 564/428; 564/433; 564/434

(58) Field of Classification Search ........... 428/690, 428/917; 313/504, 506; 564/427, 428, 433, 564/434
See application file for complete search history.

(56) References Cited

U.S. PATENT DOCUMENTS

| 5,759,444 | A | 6/1998 | Enokida et al. ...... 252/301.16 |
| 5,925,472 | A * | 7/1999 | Hu et al. .................. 428/690 |
| 6,465,115 | B2 | 10/2002 | Shi et al. .................. 428/690 |
| 2005/0249972 | A1 * | 11/2005 | Hatwar et al. ............ 428/690 |

FOREIGN PATENT DOCUMENTS

| JP | 2003267973 A * | 9/2003 |
| JP | 2004-091334 | 3/2004 |
| JP | 2004-095850 | 3/2004 |
| JP | 2004091334 A * | 3/2004 |
| JP | 2004095850 A * | 3/2004 |

OTHER PUBLICATIONS

Bull. Soc. Chim. Belg., 66, p. 413-437, (1957).*
Compt. rend. (1950), 230, p. 664-5 (with HCAPLUS database English abstract printout attached).*
Annali di Chimica Applicata (1947), 2(12), p. 739-89 (with HCAPLUS database English abstract printout attached).*
Comptes Rendus des Sciences de l'Academie des Sciences, Series C: Sciences Chimiques (1970), 271(20), p. 1258-1261 (with HCAPLUS database English abstract printout attached).*
Taiwan Office Action, no date listed.

* cited by examiner

Primary Examiner—Dawn L. Garrett
(74) Attorney, Agent, or Firm—Thomas, Kayden, Horstemeyer & Risley

(57) ABSTRACT

An anthracene compound for an organic electroluminescent device, having formula (I) or (II)

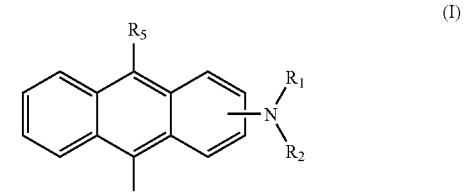

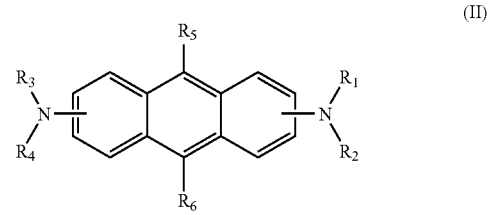

wherein $R_1$, $R_2$, $R_3$, $R_4$, $R_5$, and $R_6$ are each individually an unsubstituted or substituted aryl group having 6 to 20 carbon atoms, an unsubstituted or substituted heteroaryl group having 6 to 20 carbon atoms, or an unsubstituted or substituted alkyl group having 1 to 12 carbon atoms, wherein the substituent is $C_{1-10}$ alkyl, $C_{1-10}$ alkoxy, or halogen.

10 Claims, 1 Drawing Sheet

ANTHRACENE COMPOUND FOR ORGANIC ELECTROLUMINESCENT DEVICE

BACKGROUND OF THE INVENTION

1. Field of the Invention

The present invention relates to an anthracene compound for an organic electroluminescent device, and more particularly to an anthracene compound serving as a light-emitting layer or hole transport layer of an organic electroluminescent device.

2. Description of the Related Art

An organic electroluminescent device (also referred to as organic light-emitting diode; OLED) is an LED with an organic layer acting as the active layer, increasingly applied in flat panel displays due to advantages, such as low voltage operation, high brightness, light weight, slim profile, wide viewing angle, and highly effective contrast ratio.

Generally, an OLED is composed of a light-emitting layer and a pair of electrodes sandwiching the light-emitting layer. Light emission is caused by the following phenomenon. When an electric field is applied to these two electrodes, the cathode injects electrons into the light-emitting layer and the anode injects holes into the light-emitting layer. When the electrons recombine with the holes in the light-emitting layer, their energy level shifts to a valence bond band which causes them to release energy as fluorescent light.

Anthracene has been used as material for a hole transport layer and a light-emitting layer. For example, U.S. Pat. No. 6,465,115 discloses an organic anthracene material as the hole transport layer, having the following formula:

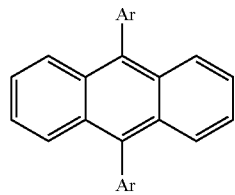

wherein Ar is individually substituted or unsubstituted aryl having 5 to 20 carbon atoms.

In U.S. Pat. No. 5,759,444, an anthracene compound emitting light is disclosed, having the following formula:

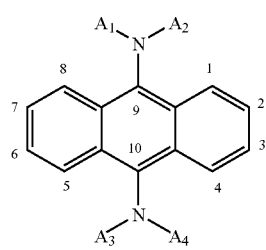

wherein each of $A_1$ to $A_4$ is a substituted or unsubstituted aryl group having 6 to 16 carbon atoms. In the anthracene compound, the diarylamino group is introduced at positions 9 and 10 of the anthracene ring. It is found that the diarylamino group causes the anthracene light-emitting material to have a hole transport property. In addition, the stability at the interface between the light-emitting layer and the hole transport layer is increased, thus increasing the life of the device.

SUMMARY OF THE INVENTION

An object of the present invention is to provide a novel anthracene compound containing a diarylamino group, diheteroarylamino group, or dialkylamino group.

Another object of the present invention is to provide an organic electroluminescent device including the anthracene compound of the present invention. The anthracene compound of the present invention can serve as a light-emitting layer or a hole transport layer in the organic electroluminescent device.

To achieve the above objects, the anthracene compound of the present invention has formula (I) or (II)

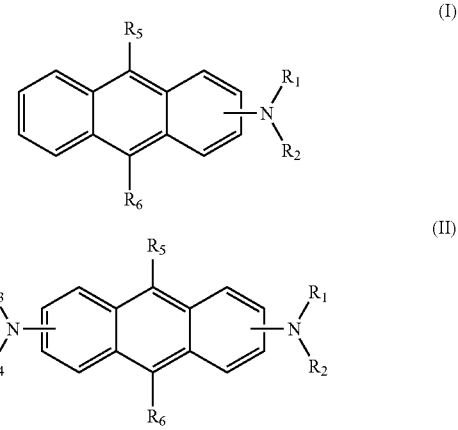

wherein $R_1$, $R_2$, $R_3$, $R_4$, $R_5$, and $R_6$ are each individually an unsubstituted or substituted aryl group having 6 to 20 carbon atoms, an unsubstituted or substituted heteroaryl group having 6 to 20 carbon atoms, or an unsubstituted or substituted alkyl group having 1 to 12 carbon atoms, wherein the substituent is $C_{1-10}$ alkyl, $C_{1-10}$ alkoxy, or halogen.

The organic electroluminescent device of the present invention includes a pair of electrodes and a layer of organic light emitting medium disposed between the pair of electrodes. The layer of organic light emitting medium includes an anthracene compound having formula (I) or (II) as above.

BRIEF DESCRIPTION OF THE DRAWING

The present invention will become more fully understood from the detailed description given hereinbelow and the accompanying drawing, given by way of illustration only and thus not intended to be limitative of the present invention.

DETAILED DESCRIPTION OF THE INVENTION

Figure 1:
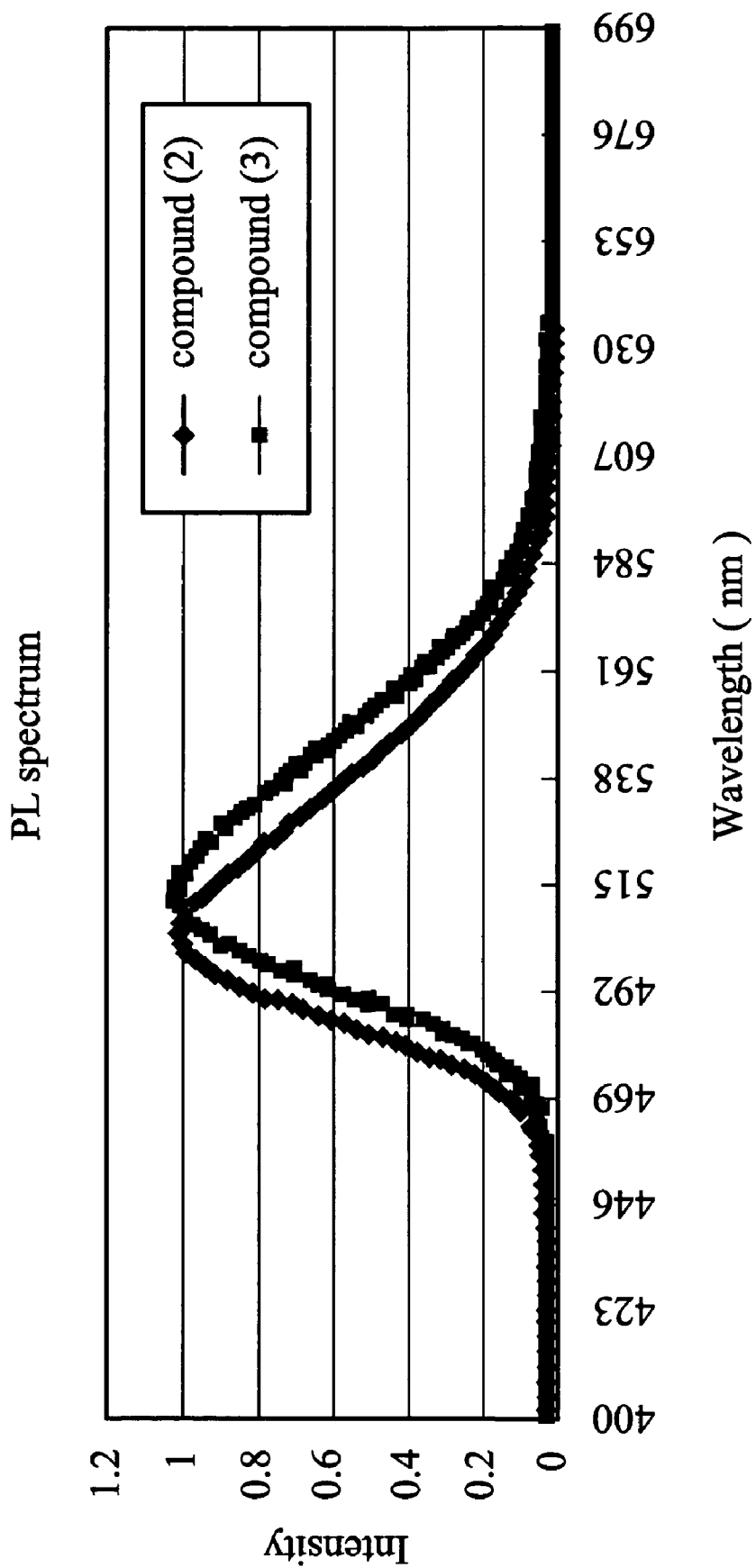
FIG. 1 is a diagram showing the photoluminescent (PL) intensity of compounds (2) and (3) at various wavelengths.

The feature of the present invention resides in that in the anthracene compound of the present invention, at least one diarylamino group (or diheteroarylamino group or dialkyamino group) is introduced at one of the positions 1 to 4 and 5 to 8 of the anthracene ring.

Specifically, one diarylamino group (or diheteroary-lamino group or dialkyamino group) can be introduced at one of the positions 1 to 4 of the anthracene ring. Thus, the anthracene compound of the present invention has formula (I)

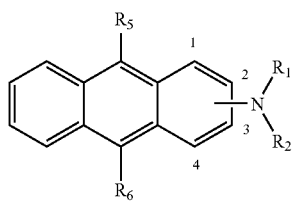

wherein $R_1$, $R_2$, $R_5$, and $R_6$ are each individually an unsubstituted or substituted aryl group having 6 to 20 carbon atoms, an unsubstituted or substituted heteroaryl group having 6 to 20 carbon atoms, or an unsubstituted or substituted alkyl group having 1 to 12 carbon atoms, wherein the substituent is $C_{1-10}$ alkyl, $C_{1-10}$ alkoxy, or halogen.

Any two of diarylamino groups, diheteroarylamino groups and dialkyamino groups can be introduced on the anthracene ring. One of the above amino groups is introduced at one of the positions 1 to 4, and the other at one of the positions 5 to 8. Thus, the anthracene compound of the present invention has formula (II)

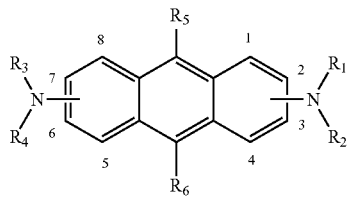

wherein $R_1$, $R_2$, $R_3$, $R_4$, $R_5$, and $R_6$ are each individually an unsubstituted or substituted aryl group having 6 to 20 carbon atoms, an unsubstituted or substituted heteroaryl group having 6 to 20 carbon atoms, or an unsubstituted or substituted alkyl group having 1 to 12 carbon atoms, wherein the substituent is $C_{1-10}$ alkyl, $C_{1-10}$ alkoxy, or halogen.

For each of $R_1$ to $R_6$ in the compounds of formulae (I) and (II), representative examples of the unsubstituted or substituted aryl groups include phenyl, 2-methylphenyl, 3-methylphenyl, 4-methylphenyl, 4-ethylphenyl, biphenyl, 4-methylbiphenyl, 4-ethylbiphenyl, 4-cyclohexylbiphenyl, terphenyl, 3,5-dichlorophenyl, naphthyl, 5-methylnaphthyl, anthryl, and pyrenyl.

Representative examples of the unsubstituted or substituted heteroaryl groups include furanyl, thiophenyl, pyrrolyl, pyranyl, thiopyranyl, pyridinyl, thiazolyl, imidazolyl, pyrimidinyl, triazinyl, indolyl, quinolyl, purinyl and carbazolyl.

Representative examples of the unsubstituted or substituted alkyl groups include methyl, ethyl, propyl, butyl, sec-butyl, tert-butyl, pentyl, hexyl, heptyl, octyl, stearyl, 2-phenylisopropyl, trichloromethyl, and trifluoromethyl.

When only one diarylamino group (or diheteroarylamino group or dialkylamino group) is introduced at position 2 of the anthracene ring, the anthracene compound of the present invention has formula (III)

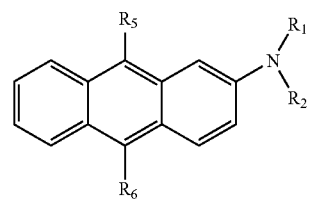

wherein $R_1$, $R_2$, $R_5$, and $R_6$ are defined above.

When $R_1$ and $R_2$ are unsubstituted or substituted aryl groups, representative examples of formula (III) include

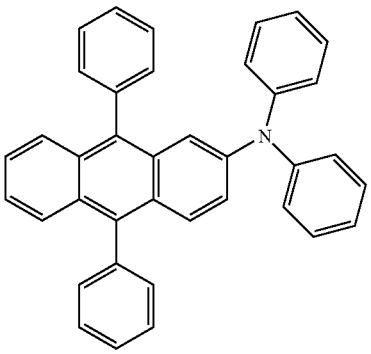

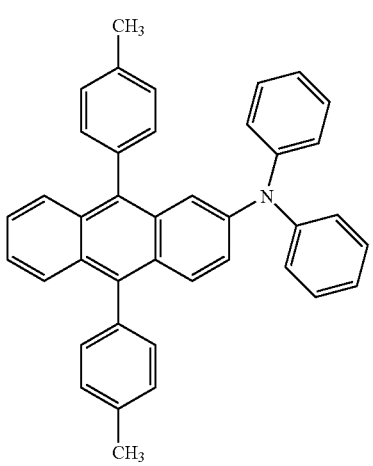

-continued

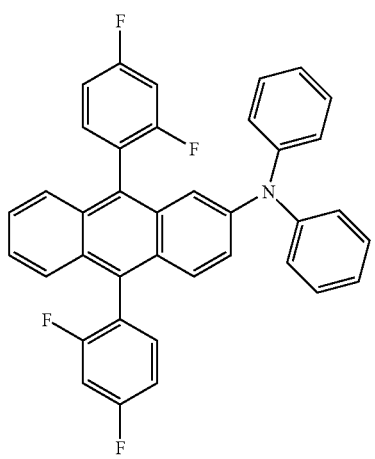

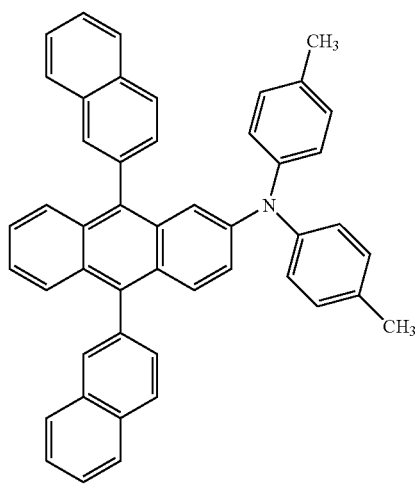

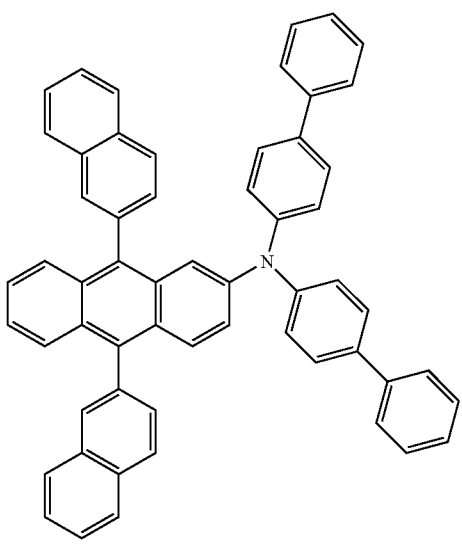

-continued

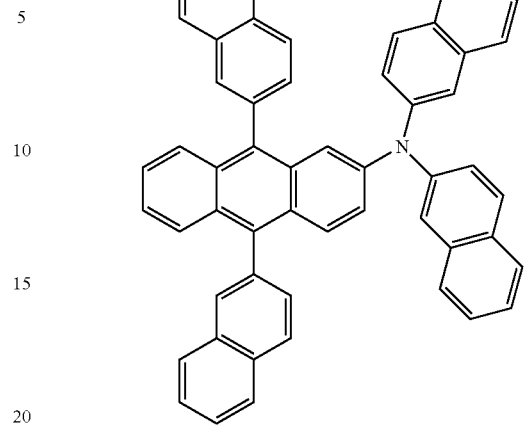

When one diarylamino group (or diheteroarylamino group or dialkylamino group) is introduced at position 2 and the other diarylamino group (or diheteroarylamino group or dialkylamino group) at position 6 of the anthracene ring, the anthracene compound of the present invention has formula (IV)

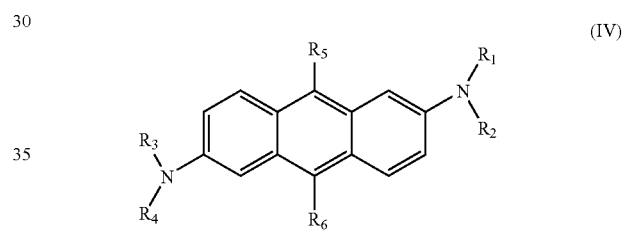

(IV)

wherein $R_1$, $R_2$, $R_3$, $R_4$, $R_5$, and $R_6$ are defined above.
When $R_1$ to $R_4$ are unsubstituted or substituted aryl group, representative examples of formula (IV) include

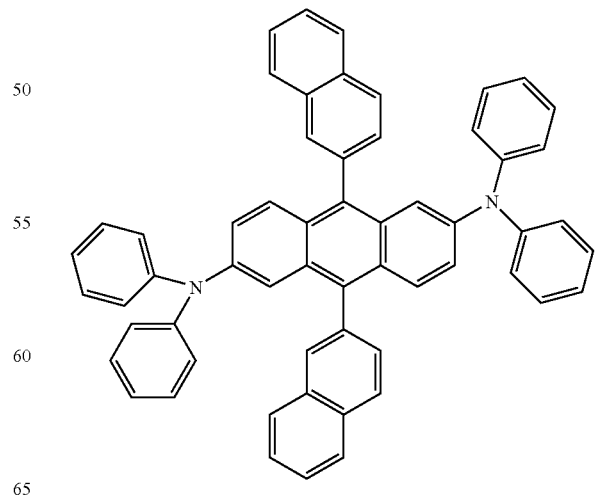

-continued
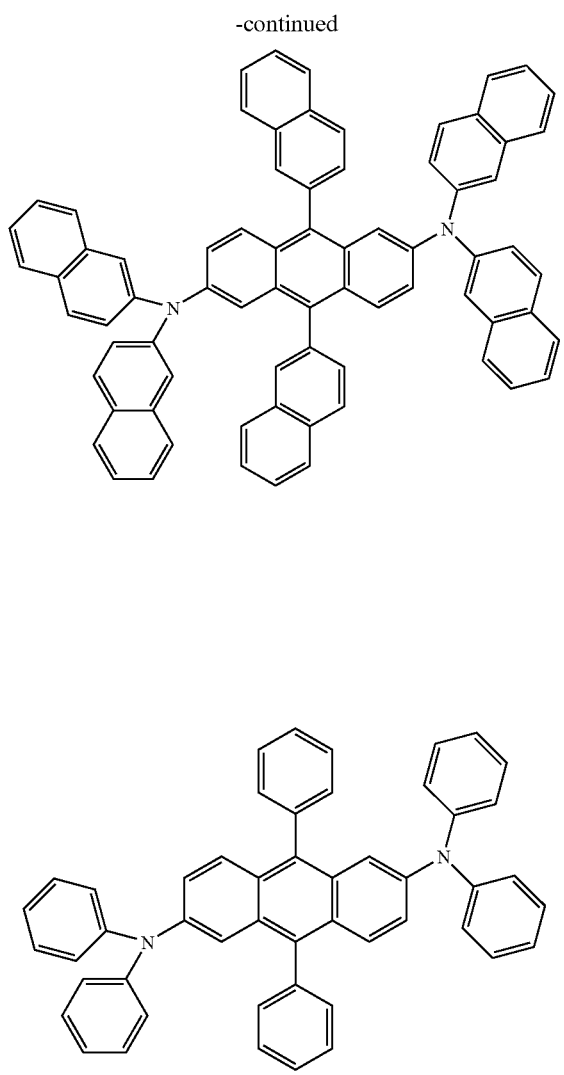
-continued
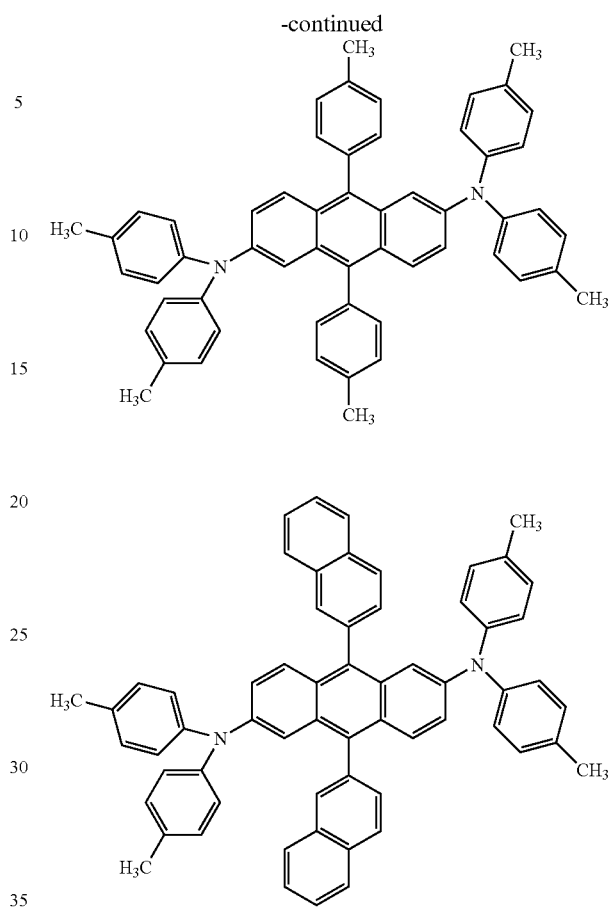
The following examples are intended to illustrate the process and the advantages of the present invention without limiting its scope, since numerous modifications and variations will be apparent to those skilled in the art.
EXAMPLE 1
The synthesis pathway is shown below.
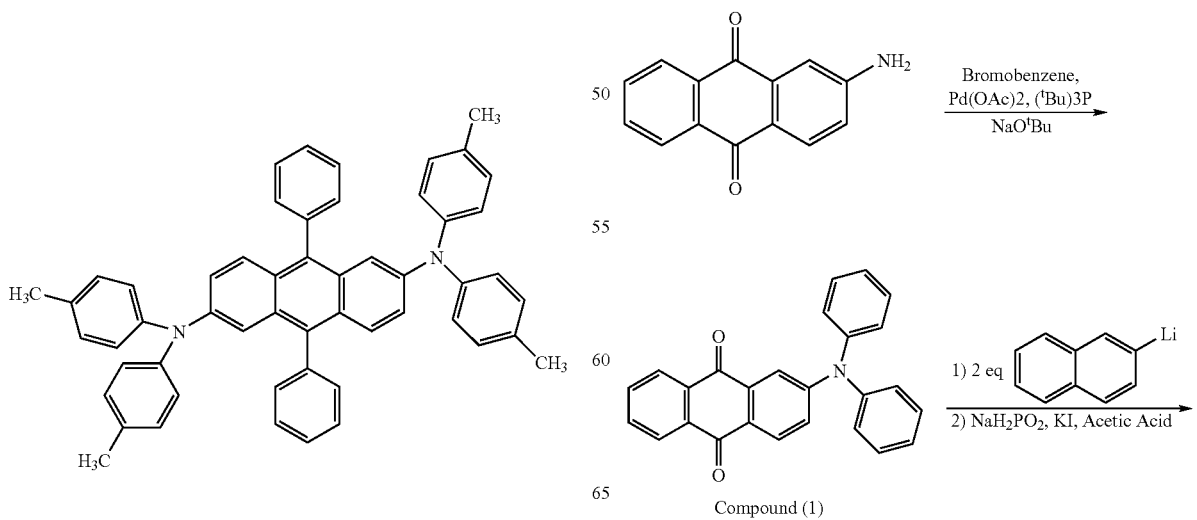
Compound (1)

-continued

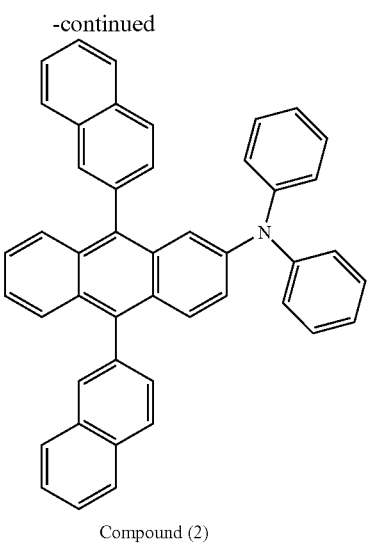

Compound (2)

Method of Synthesis of Compound (1)

To a suspension of anthraquinone (1 g, 4.8 mmol), bromobenzene (1.66 g, 10.6 mmol), NaOtBu (1.1 g, 11.52 mmol) and Pd(OAc)$_2$ (71 mg, 0.32 mmol) were dissolved in 50 mL dry toluene, tri-tert-butylphosphine (257 mg, 1.28 mmol) was added through a syringe. The reaction mixture was heated to reflux for 36 hours. After cooling, the reaction was added with 50 mL of water, then extracted with ethyl acetate. After being dried over MgSO$_4$, and then purified by column chromatography to give the compound (1) (1.04 g).

Method of Synthesis of Compound (2)

2-Bromonaphthalene (2.3 g, 11 mmole) was dissolved in 100 mL THF, the 4.8 mL n-BuLi (11 mmol, 2.5M) was slowly added into the solution at −78° C. After 30 minutes, the above mixture was added to the compound (1) (1.7 g, 4.7 mmol) in 30 mL THF dropwise at −78° C. The mixture was left to reach room temperature. Cold water (100 mL) was added and the organic phase separated. The water phase was extracted with ethyl acetate. The organic fractions were dried over MgSO$_4$, and then the solvent was removed by a rotary evaporator. KI (2.8 g, 17 mmole), sodium hypophosphite monohydrate (3.8 g, 32 mmole), and 30 mL acetic acid were added to the crude residue. The mixture was heated under reflux for 2 hours. After cooling, the white precipitate was collected, then purified by column chromatography to give the compound (2) (2.5 g).

FIG. 1 is a diagram showing the photoluminescent (PL) intensity of compounds (2) and (3) at various wavelengths. It shows that for compound (2), the wavelength at the maximum intensity is 504 nm, indicating that compound (2) emits green light.

In addition, the HOMO level of compound (2) was measured to be 5.40 eV, which is very close to the HOMO level (5.5 eV) of NPB (a commonly-used material for the hole transport layer). Thus, compound (2) of the present invention is suitable for use as a hole transport layer.

EXAMPLE 2

Method of Synthesis of Compound (3)

The synthesis pathway is shown below.

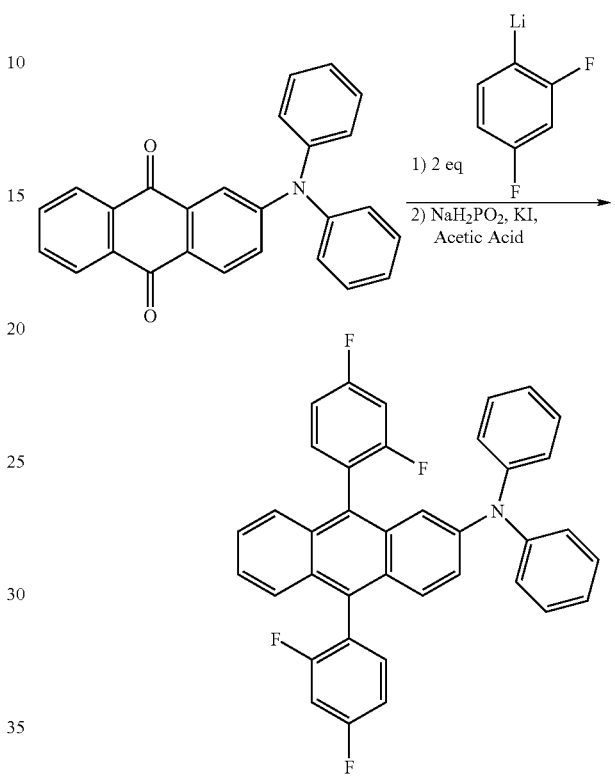

Compound (3)

2,4-difluorobromobenzene (2.5 g, 13 mmole) was dissolved in 100 mL THF, and 5.2 mL nBuLi (13 mmol, 2.5M) was then slowly added into the mixture at −78° C. After 30 minutes, the above mixture was added to the compound (1) (2.1 g, 5.8 mmol) in 30 mL THF dropwise at −78° C. The mixture was left to reach room temperature. Cold water (100 mL) was added and the organic phase was separated. The water phase was extracted with ethyl acetate. The organic fractions were dried over MgSO$_4$ and the solvent was then removed by rotary evaporator. KI (3.4 g, 20.5 mmole), sodium hypophosphite monohydrate (4.9 g, 41.2 mmole), and 30 mL acetic acid were added to the crude residue. The mixture was heated under reflux for 2 hours. After cooling, the white precipitate was collected, then purified by column chromatography to give the compound (3) (1.6 g).

FIG. 1 is a diagram showing the photoluminescent (PL) intensity of compounds (2) and (3) at various wavelengths. It shows that for compound (3), the wavelength at the maximum intensity is 513 nm, indicating that compound (3) emits green light.

In addition, the HOMO level of compound (3) was measured to be 5.85 eV, which is very close to the HOMO level (5.5 eV) of NPB (a commonly-used material for the hole transport layer). Thus, compound (3) of the present invention is suitable for use as a hole transport layer.

EXAMPLE 3

Method of Synthesis of Compound (4)
The synthesis pathway is shown below.

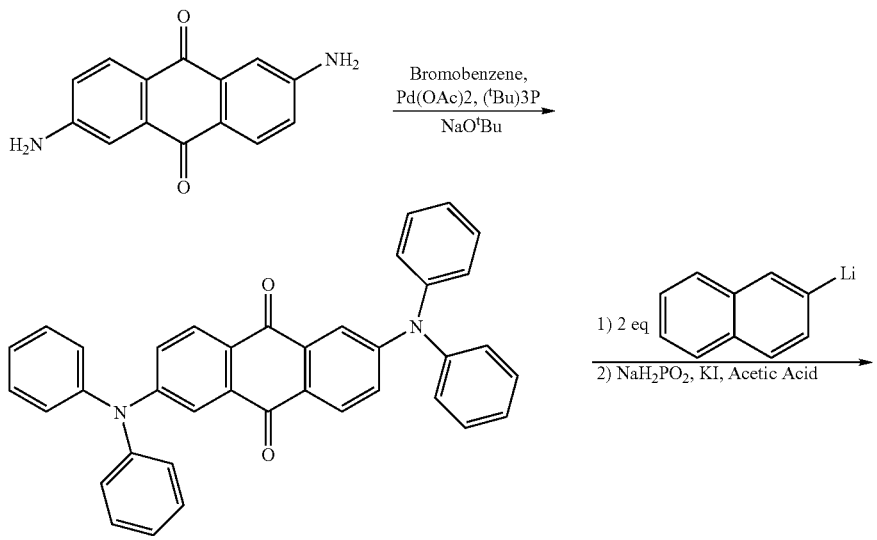

Compound (4)

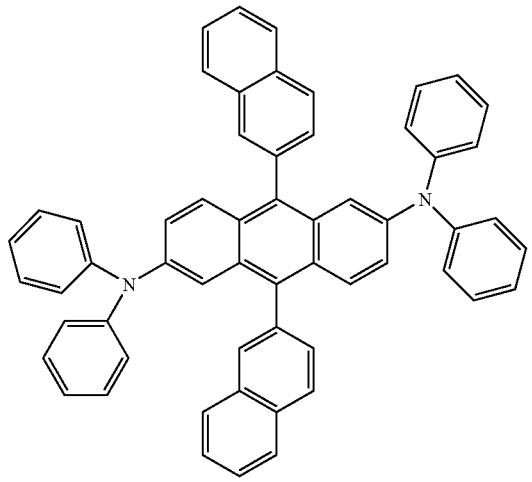

Compound (5)

To a suspension of 2,6-diaminoanthraquinone (1.2 g, 5 mmol), bromobenzene (3.5 g, 22 mmol), NaOtBu (1.2 g, 12 mmol) and Pd(OAc)$_2$ (149 mg, 0.66 mmol) were dissolved in 50 mL dry toluene, tri-tert-butylphosphine (533 mg, 2.64 mmol) was added through a syringe. The reaction mixture was heated to reflux for 36 hours. After cooling, the reaction mixture was added with 50 mL water, then extracted with ethyl acetate. After dry over MgSO$_4$, the reaction mixture was purified by column chromatography to give the compound (4) (1.1 g).

Method of Synthesis of Compound (5)

2-Bromonaphthalene (2.3 g, 11 mmole) was dissolved in 100 mL THF, then 4.8 mL nBuLi (11 mmol, 2.5M) was slowly added into the mixture at −78° C. After 30 minutes, the compound (4) (2.7 g, 5 mmol) in 30 mL THF was added dropwise at −78° C. The mixture was left to reach room temperature. Cold water (100 mL) was added and the organic phase was separated. The water phase was extracted with ethyl acetate. The organic fractions were dried over MgSO$_4$ then the solvent was removed by rotary evaporator. KI (3.0 g, 18 mmole), sodium hypophosphite monohydrate (4.1 g, 34 mmole), and 30 mL acetic acid were added to the crude residue. The mixture was heated under reflux for 2 hours. After cooling, the white precipitate was collected, then purified by column chromatography to give compound (5) (3.1 g).

The foregoing description of the preferred embodiments of this invention has been presented for purposes of illustration and description. Obvious modifications or variations are possible in light of the above teaching. The embodiments chosen and described provide an excellent illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. An anthracene compound having formula (I)

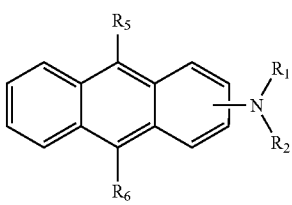

wherein $R_1$, and $R_2$, are each individually an unsubstituted or substituted aryl group having 6 to 20 carbon atoms, an unsubstituted or substituted heteroaryl group having 6 to 20 carbon atoms, wherein the substituent is $C_{1-10}$ alkyl, $C_{1-10}$ alkoxy, or halogen; and $R_5$, and $R_6$ are each individually an unsubstituted or substituted phenyl group, an unsubstituted or substituted heteroaryl group having 6 to 20 carbon atoms, or an unsubstituted or substituted alkyl group having 1 to 12 carbon atoms, wherein the substituent is $C_{1-10}$ alkyl, $C_{1-10}$ alkoxy, or halogen.

2. The anthracene compound as claimed in claim 1, which has formula (III)

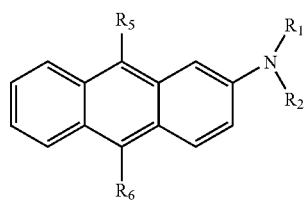

wherein $R_1$, $R_2$, $R_5$, and $R_6$ are defined above.

3. The anthracene compound as claimed in claim 2, which is selected from the following formulae

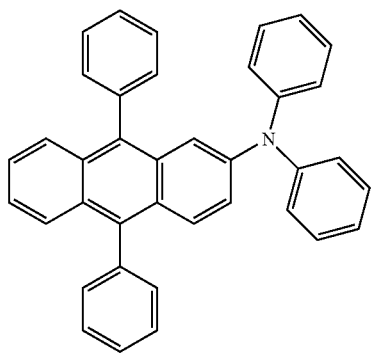

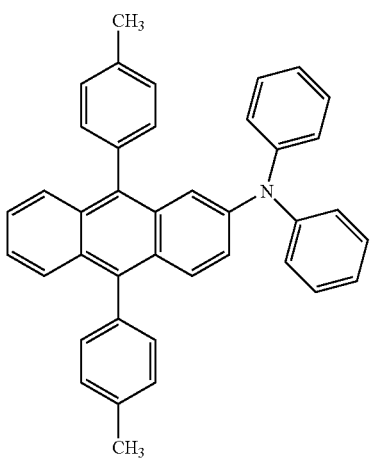

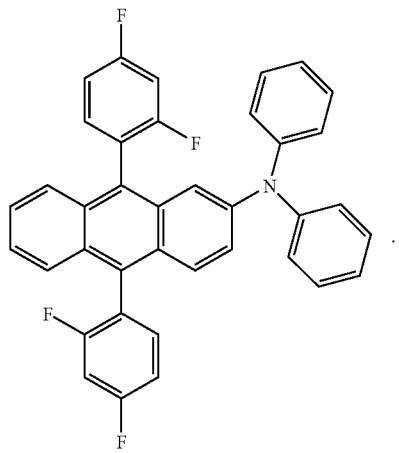

4. The anthracene compound as claimed in claim 1, which is light emitting.

5. The anthracene compound as claimed in claim 1, which has hole transport property.

6. An organic electroluminescent device, comprising a pair of electrodes and a layer of organic light emitting medium disposed between the pair of electrodes, wherein the layer of organic light emitting medium includes an anthracene compound having formula (I)

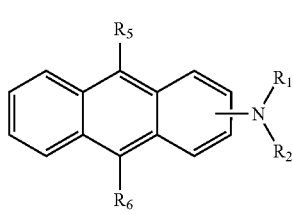

wherein $R_1$, and $R_2$, are each individually an unsubstituted or substituted aryl group having 6 to 20 carbon atoms, an unsubstituted or substituted heteroaryl group having 6 to 20 carbon atoms, wherein the substituent is $C_{1-10}$ alkyl, $C_{1-10}$ alkoxy, or halogen; and $R_5$, and $R_6$ are each individually an unsubstituted or substituted phenyl group, an unsubstituted or substituted heteroaryl group having 6 to 20 carbon atoms, or an unsubstituted or substituted alkyl group having 1 to 12 carbon atoms, wherein the substituent is $C_{1-10}$ alkyl, $C_{1-10}$ alkoxy or halogen.

7. The organic electroluminescent device as claimed in claim 6, wherein the anthracene compound has formula (III)

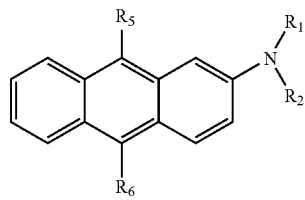
(III)

wherein $R_1$, $R_2$, $R_5$, and $R_6$ are defined above.

8. The organic electroluminescent device as claimed in claim 7, wherein the anthracene compound is selected from the following formulae

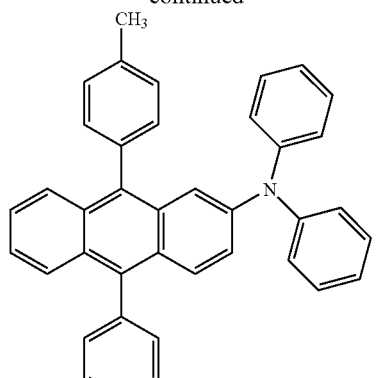

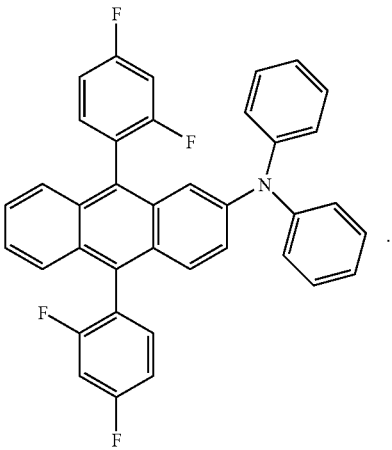

9. The organic electroluminescent device as claimed in claim 6, wherein the layer of organic light emitting medium includes a light emitting layer, and the light emitting layer includes an anthracene compound having formula (I).

10. The organic electroluminescent device as claimed in claim 6, wherein the layer of organic light emitting medium includes a light emitting layer and a hole transport layer, and the hole transport layer includes an anthracene compound having formula (I).

* * * * *